(12) United States Patent
Ringermacher et al.

(10) Patent No.: US 7,409,313 B2
(45) Date of Patent: Aug. 5, 2008

(54) METHOD AND APPARATUS FOR NONDESTRUCTIVE EVALUATION OF INSULATIVE COATING

(75) Inventors: Harry Israel Ringermacher, Delanson, NY (US); Elena Rozier, Schenectady, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 11/305,438

(22) Filed: Dec. 16, 2005

(65) Prior Publication Data

US 2007/0143061 A1 Jun. 21, 2007

(51) Int. Cl.
 *G01B 11/02* (2006.01)
 *G01B 15/02* (2006.01)
 *G01N 25/18* (2006.01)

(52) U.S. Cl. .................. 702/172; 702/136; 702/134; 250/390.06; 250/559.27; 374/44

(58) Field of Classification Search ................ 702/130, 702/132, 134–136, 155, 158, 159, 170, 172; 250/390.06, 559.12, 559.27, 559.28; 356/496, 356/503, 504, 630, 632; 374/9, 43, 44
See application file for complete search history.

(56) References Cited

U.S. PATENT DOCUMENTS

| | | | |
|---|---|---|---|
| 4,768,158 A | | 8/1988 | Osanai |
| 4,792,683 A | | 12/1988 | Chang et al. |
| 4,854,724 A | | 8/1989 | Adams et al. |
| 4,928,254 A | * | 5/1990 | Knudsen et al. ............. 702/136 |
| 5,032,727 A | | 7/1991 | Cox, Jr. et al. |
| 5,073,433 A | * | 12/1991 | Taylor ................. 428/134 |
| 5,201,582 A | | 4/1993 | Lesniak |
| 5,246,291 A | | 9/1993 | Lebeau et al. |
| 5,250,809 A | | 10/1993 | Nakata et al. |
| 5,292,195 A | | 3/1994 | Crisman, Jr. |
| 5,539,656 A | | 7/1996 | Annigeri et al. |
| 5,564,830 A | * | 10/1996 | Bobel et al. ................. 374/126 |

(Continued)

FOREIGN PATENT DOCUMENTS

DE 19520788 8/2001

(Continued)

OTHER PUBLICATIONS

S K Lau, D P Almond, and P M Patel; Transient Thermal Wave Techniques for the Evaluation of Surface Coatings; School of Materials Science, University of Bath, Claverton Down, Bath BA2 7AY, UK; Nov. 26, 1990; pp. 428-436.

(Continued)

*Primary Examiner*—Manuel L Barbee
(74) *Attorney, Agent, or Firm*—Fletcher Yoder

(57) ABSTRACT

An apparatus is provided for determining thickness and thermal conductivity for an insulative coating disposed on a substrate in an object. The apparatus includes a source for rapidly applying a multiple optical pulses on a surface of the object, where the surface comprises the insulative coating. The system further includes a recording system configured to collect data representative of the propagation of the optical pulses in the object. The apparatus further includes a processor coupled to the recording system and configured to receive the data from the recording system and configured to determine a thickness value and a thermal conductivity value for the insulative coating.

38 Claims, 3 Drawing Sheets

U.S. PATENT DOCUMENTS

| | | | |
|---|---|---|---|
| 5,582,485 A | 12/1996 | Lesniak | |
| 5,631,465 A | 5/1997 | Shepard | |
| 5,683,181 A | 11/1997 | Shepard | |
| 5,711,603 A | 1/1998 | Ringermacher et al. | |
| 6,515,284 B1 | 2/2003 | Walle et al. | |
| 2003/0138025 A1* | 7/2003 | Archibald et al. | 374/6 |

FOREIGN PATENT DOCUMENTS

| | | |
|---|---|---|
| EP | 304708 | 3/1989 |
| GB | 2168494 | 6/1986 |
| GB | 2220065 | 12/1989 |
| JP | 10274675 | 10/1998 |
| WO | WO9805921 | 2/1998 |
| WO | WO9805949 | 2/1998 |

OTHER PUBLICATIONS

A Mogro-Campero and R Annigeri; Thermal conductivity of Class B TBC as a Function of Aging Time and Temperature; CRD Ceramic Technologies; GEPS, Greenville, SC; 13 pages.

* cited by examiner

METHOD AND APPARATUS FOR NONDESTRUCTIVE EVALUATION OF INSULATIVE COATING

BACKGROUND

The present invention in accordance with certain embodiments, relates to a nondestructive testing technique for determining thickness, as well as conductivity of an insulative coating. More particularly, the present invention provides a high-speed infrared transient thermography method and apparatus for measuring thickness and conductivity for an insulative coating.

Over the years, various nondestructive ultrasonic measurement techniques have been utilized to determine the cross-sectional thickness of cast metal or other solid objects. Unfortunately, conducting ultrasonic measurements to examine the cross-sectional thickness generally necessitates a cumbersome and time-consuming mechanical scanning of the entire surface with a transducer. In addition, to facilitate intimate sonic contact between the transducer and the object surface to provide proper propagation of ultrasonic waves into the object, a stream of liquid couplant must be applied to the surface, or, alternatively, total immersion of the object in the couplant must be accommodated. Such accommodations, however, are not practical or even feasible for numerous structural and material reasons. Moreover, ultrasonic systems capable of scanning and analyzing geometrically complex parts are typically very expensive and complicated. In addition, a mechanical scanning of the transducer over the surface of a large object can be a time consuming process, increasing costs and production times.

In contrast, infrared (IR) transient thermography is a somewhat more versatile nondestructive testing technique that relies upon temporal measurements of heat transference through an object to provide information concerning the structure and integrity of the object. Heat flow through an object is substantially unaffected by the micro-structure and the single-crystal orientations of the material of the object, therefore, an infrared transient thermography analysis is essentially free of the limitations this creates for ultrasonic measurements. Additionally, transient thermographic analysis approach is not significantly hampered by the size, contour or shape of the object being tested and, moreover, can be accomplished ten to one-hundred times faster than most conventional ultrasonic methods, particularly when testing objects with large surface areas.

Conventionally, an infrared (IR) video camera has been used to record and store successive thermal images (frames) of an object surface after heating it. Each video image is composed of a fixed number of pixels, each pixel representing a small picture element in an image array or frame. Each pixel corresponds to a rectangular area, called a resolution element, on the surface of the object being imaged. Because, the temperature at each resolution element is directly related to the intensity of the corresponding pixel, temperature changes at each resolution element on the object surface can be analyzed in terms of changes in pixel contrast.

One known contemporary application of transient thermography is the ability to determine the size and relative location (depth) of flaws within solid non-metal composites; another application of transient thermography is for determining the thickness of metal objects. Some attempts have been recently made to measure the thickness of insulative coating as well. These include modeling techniques where the insulative coating thickness may be obtained by fitting the coating data to a model and comparing it with known thickness standards. Unfortunately, these techniques include point-by-point measurement of the coating thickness, and therefore take time and are complex computationally. Another aspect to thickness measurement for insulative coatings is that as the coating ages the thermal conductivity of the coating changes and affects the thickness of the coating. Therefore, there is also a need for determining the thermal conductivity as well for the insulative coating for accurate thickness measurement.

Therefore, there is a need for a technique that can measure quantitatively, the absolute thickness for insulative coating without using the thickness standards.

BRIEF DESCRIPTION

According to one aspect of the present invention, an apparatus is provided for determining thickness and thermal conductivity for an insulative coating disposed on a substrate in an object. The apparatus includes a source for rapidly applying multiple optical pulses on a surface of the object, where the surface comprises the insulative coating. The system further includes a recording system configured to collect data representative of the propagation of the optical pulses in the object. The apparatus further includes a processor coupled to the recording system and configured to receive the data from the recording system and configured to determine a thickness value and a thermal conductivity value for the insulative coating.

According to another aspect of the present technique, a method for determining thickness and thermal conductivity for an insulative coating is provided. The method includes obtaining a respective time-temperature response for the insulative coating and for a substrate, where the insulative coating is disposed on the substrate. The method also includes measuring a deltalog value and measuring an inflection point value from the respective time-temperature response for the coating and for the substrate. The method further includes calculating one or more coating characteristic values using the deltalog value or the inflection point value. The method lastly includes determining a thermal conductivity value or a coating thickness value using one or more of the coating characteristic values.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

By way of example, the present invention relates to non-destructive testing methods and apparatus for determining and displaying the actual thickness and the thermal conductivity value of an insulative coating through the use of high-speed infrared (IR) transient thermography.

Figure 1:
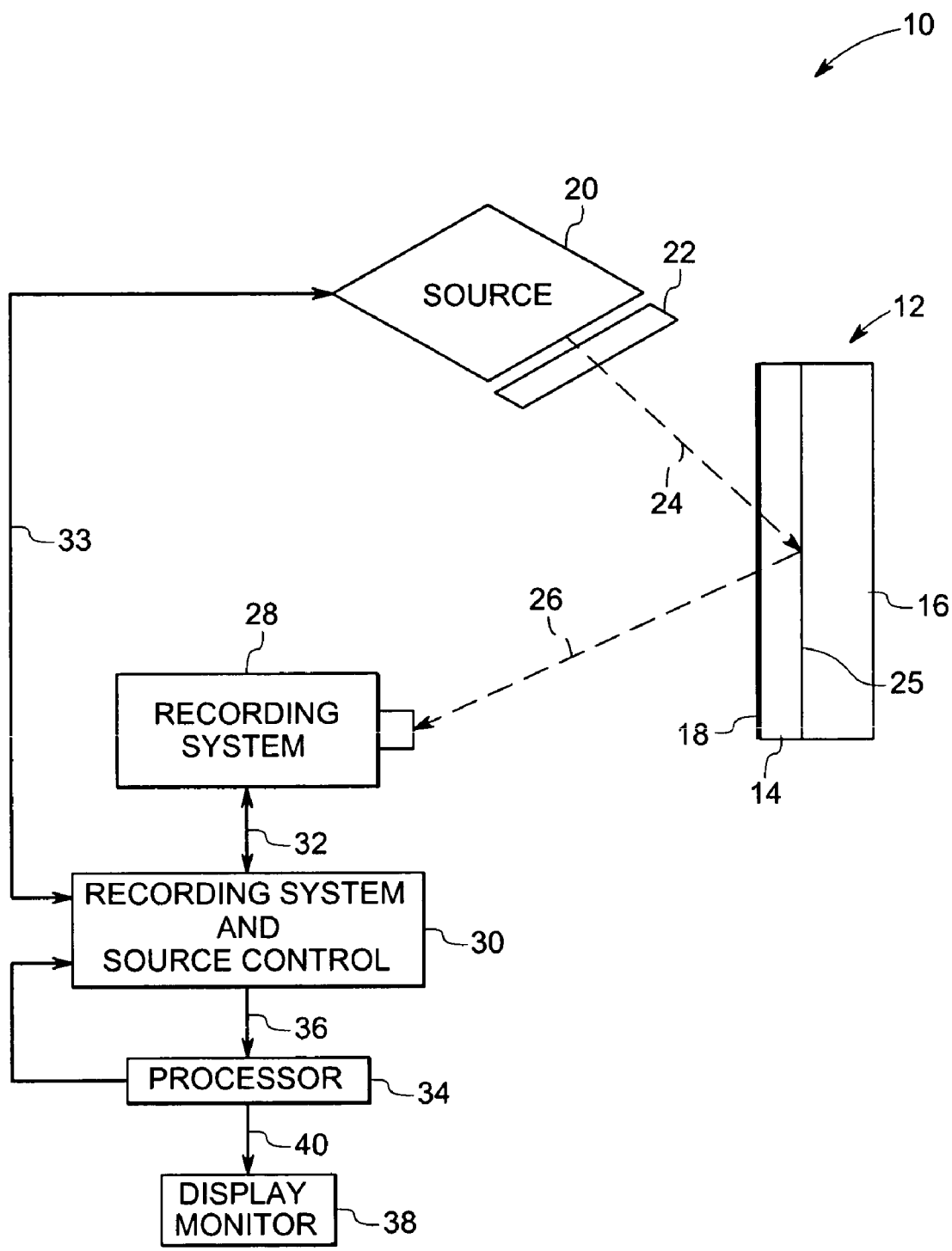
FIG. 1 is a diagrammatic representation of an exemplary infrared transient thermography system for determining and displaying the thickness and thermal conductivity of an insulative coating, in accordance with an aspect of the present invention.

FIG. 1 is a diagrammatic representation of an apparatus 10 for determining thickness and thermal conductivity for an object 12. More specifically, the exemplary apparatus of FIG. 1 can be used to determine the thickness and thermal conductivity of an insulative coating 14 disposed on a substrate 16 of the object 12. The substrate 16 is a thermally conductive substrate in one example. The coating 14 in one example is a thermal barrier coating (TBC), and in another example the coating 14 is an environment barrier coating (EBC). The object 12 in one example includes a dark peripheral coating 18 disposed over the insulative coating 14 for effective imaging. In one example, a carbon spray that is essentially soot and that dries quickly upon application is used as the dark peripheral coating 18. The object 12, in another example is first painted (e.g., by spray, brush or roller) with a thin quick-drying coating 18 of a high-ultraviolet, visible light, and infrared-absorbency substance, such as, a carbon-based material such as graphite, carbon, or carbon-black water-based paint. It will be appreciated by those skilled in the art that the dark peripheral coating does not alter any characteristics of the insulative coating 14 and can be burned off in air separately or upon first cycle at operating temperature.

The apparatus 10 also includes a source 20 for rapidly applying multiple optical pulses 24 on the surface of the object 12, where the surface includes the insulative coating 14. In one example, the source 20 includes one or more flash lamps that flash high power optical pulses at the surface of the object 12. In the exemplary embodiment, a flash-lamp heat-pulse source 20 is triggered to rapidly heat the surface of the object 12 being measured. One suitable arrangement for flash-lamp heat-pulse source 20 is, for example, a set of four or eight high-speed, high output power photographic flash-lamps, each capable of about 4.8 Kilo-joules output and having individual power supplies (such as manufactured by Speedotron, Corp. of Chicago, Ill.).

The apparatus 10 in a specific example includes a filter 22 disposed between the source 20 and the object 12 and is configured to eliminate optical wavelength greater than about two micron emanating from the source 20. In one example, the flash-lamp filter 22 may be comprised of Pyrex® glass (Corning Inc.), fused quartz, BK7 (BK7 is a borosilicate crown glass that is used extensively for lenses, windows, and mirror substrates), or other optical material that is transparent to visible and UV (ultra violet) light and is coated on the flash—lamp facing side with an infrared—reflective coating to reflect all radiation in the 3-5 micron range back into the flash-lamps. Optical glass and coated filters may be acquired or specially manufactured by a general scientific optics and optical glass manufacturer such as Oriel of Strafford, Conn.

Once an optical pulse or multiple pulses, which are shown generally by reference numeral 24, are applied on the dark surface 18, a thermal pulse or multiple thermal pulses propagate into the coating and are reflected off the coating/substrate interface 25. The reflected waves are shown generally by reference numeral 26.

The apparatus 10 further includes a recording system 28 configured to collect the reflected waves 26 that include data representative of the propagation of the thermal pulses in the object 12. In one example, a high speed IR focal plane array camera is used as the recording system 28 for monitoring and imaging the temperature or thermal profile in the object 12. It may be noted that the IR camera (e.g., a Radiance HS camera available from Amber Engineering of Goleta, Calif.—a Raytheon Company) captures the thermal or temperature profiles on the same side of the object 12 as the application of optical pulses by the flash or source 20. In the exemplary embodiment, the apparatus 10 uses an infrared transient thermography imaging method to receive thermal images that represent the propagation of thermal pulses in the object 12 and are captured by the recording system 28.

The apparatus 10 also includes a recording system and source control 30 for communicating with the recording system 28 and the source 20 via communication links 32 and 33 respectively. In another example, the recording system and source control 30 is included within the recording system 28. Acquisition of thermal data is preferably initiated at the time of flash lamp firing either by optical triggering or by other suitable means. Flash-lamp firing is controlled via conventional flash-lamp electronics shown as the recording system and source control 30 managed by conventional video frame acquisition software running on system computer or a processor 34 (such as provided by the ImageDesk® frame acquisition system from Amber Corp., or other conventional frame acquisition and flash-lamp control software, for example, such as commercially available from Thermal Wave Imaging Inc. of Lathrup Village, Mich.).

The system control computer/image processor 34 in one example is a programmed general-purpose digital computer that is capable of peripheral equipment control and communication functions in addition to digital image processing and display. The processor 34 controls the recording system and source control 30 to acquire a predetermined number of successive thermal image frames of the object surface, which are stored in memory (not shown) for future analysis.

The processor 34 is configured to receive the data 36 from the recording system 28 or the recording system and source control 30. The processor 34 is further configured to determine a thickness value and a thermal conductivity value for the insulative coating. To do so, the processor 34 is further configured to obtain time-temperature response for the coating 14 and the substrate 16 from the data 26 received by the recording system 28. The processor in one example is configured to measure a deltalog value and an inflection point value from the respective time-temperature response. These values are described in more detail with reference to equations herein below. The processor 34 is configured further for calculating one or more coating characteristic values using the deltalog value or the inflection point value. Some of the values calculated by the processor include, for example, a coating effusivity value, a reflectivity value, a variable, a coating characteristic time, or a thermal diffusivity value. One or more of these values are used to determine the thickness value and the thermal conductivity value of the insulative coating as per the equations herein below. In one specific example, the processor 34 is configured to determine the thickness value and the thermal conductivity value simultaneously i.e. the output of the processor includes both the thickness value and the conductivity value.

The apparatus 10 in one example also includes a display monitor 38 to receive and display an output 40 from the processor 34. The display monitor may be connected to a printer or any other device for displaying the output from the processor 34.

In order to determine the thermal conductivity value and the thickness value for the coating from the measured data as obtained from recording system 28, certain calculations are undertaken by the processor 34 as described in the following equations. It will be appreciated by those skilled in the art that the density, p, and specific heat, $c_c$, of the coating do not vary significantly upon aging. The product of these two values as shown by equation (1) is therefore taken to be constant and determined separately before the inspection $$\rho c_c = \text{constant} \tag{1}$$

As explained with reference to FIG. 1, the thermal waves penetrate the coating and are reflected off the coating/substrate interface, with a reflection coefficient or reflectivity value, R given by equation (2):

$$R = \frac{E_c - E_s}{E_c + E_s} \tag{2}$$

where $E_c$ and $E_s$ are respectively the coating and substrate "effusivity" given by:

$$E_c = \sqrt{K_c \rho c_c} \quad E_s = \sqrt{K_s \rho c_s} \tag{3}$$

where $K_c$ is the thermal conductivity for the coating and $K_s$ is the thermal conductivity for the substrate. In one example, the units for measuring include $g/cm^3$ for density ($\rho$), $cal/g-°C$ for specific heat c and $cal/s-cm-°C$ for thermal conductivity.

The temperature-time response of the coating/substrate system at the surface of the coating, following the flash, is given by:

$$T(t) = \left(1 + 2\sum_{n=1}^{\infty} R^n e^{-n^2 \frac{\tau_c}{t}}\right) T_{1/2c}(t) \tag{4}$$

where $T_{1/2c}$ is a "half-space" response of the coating to the flash pulse, given by equation (6), $\tau_c$ is the "characteristic time" of the coating of thickness L and thermal diffusivity $\alpha_c$ given by:

$$\tau_c = \frac{L^2}{\alpha_c} \tag{5}$$

The half-space function, shown in equations (6) and (7) is a "one over root-time" temperature response to a thermal impulse at the surface of an infinite "half-space" of coating or substrate. The response function as shown by equation (4) moves from the coating half-space shown by equation (6) at t=0 to the substrate half-space shown by equation (7) at t=∞.

$$T(t) \to T_{1/2c}(t) = \frac{1.1284I}{2E_c\sqrt{t}} \quad t \to 0 \tag{6}$$

$$T(t) \to T_{1/2s}(t) = \frac{1.1284I}{2E_s\sqrt{t}} \quad t \to \infty \tag{7}$$

This is easily shown by taking the infinite sum in equation (4) in the limits as t–>0 and t–>∞ using the definition of R from equation (2).

In one example, the log difference near t=0 is defined as "deltalog":

$$\text{deltalog} = \log[T_{coating}(t=0)] - \log[T_{substrate}(t=0)]. \tag{8}$$

Then we define, from equations (6) and (7), the ratio of the coating effusivity to the substrate effusivity in terms of delta-log:

$$\frac{E_c}{E_s} = 10^{-deltalog}. \tag{9}$$

The reflectivity value can also be defined from deltalog:

$$R = \frac{1 - 10^{deltalog}}{1 + 10^{deltalog}} \tag{10}$$

The inflection point, in time, can be derived theoretically by differentiating the T-t curve shown by equation (4), and setting the result to zero. Then an equation (12) given below is solved to find the point in time of maximum slope (inflection time, "$t_{inflection}$") by using a variable "p".

It may be noted by those skilled in the art that "p" is defined from:

$$p \equiv \frac{\tau_c}{t_{inflection}} \text{ or } \tau_c = p t_{inflection}, \tag{11}$$

where $\tau_c$ is the coating characteristic time.

An equation to be solved for "p" is given by:

$$p\left[\frac{\sum_{n=1}^{3} R^n n^4 e^{-n^2 p}}{\sum_{n=1}^{3} R^n n^2 e^{-n^2 p}}\right] - 2p\left[\frac{\sum_{n=1}^{3} R^n n^2 e^{-n^2 p}}{1 + 2\sum_{n=1}^{3} R^n e^{-n^2 p}}\right] - 1 = 0 \tag{12}$$

As it will be appreciated by those skilled in the art, an input to equation (12) is the experimental value R, which is obtained from equation (10). Having found the variable "p" from equation (12), the inflection point or inflection time "$t_{inflection}$" of the T-t curve is obtained experimentally by differentiating the curve and locating the maximum in time. That inflection time is then used in equation (11) to determine the coating characteristic time $\tau_c$.

The thermal diffusivity for the coating, $\alpha_c$, is defined as:

$$\alpha_c \equiv \frac{K_c}{\rho c_c} \tag{13}$$

Thermal conductivity $K_c$ is found from the definition of coating effusivity in equation (3):

$$K_c = \frac{E_c^2}{\rho c_c} \tag{14}$$

since $\rho c_c$ is known from (1) and $E_c$ from equation (9), we can determine $\alpha_c$ as given by equation (13).

Finally the coating thickness, L, is then found from equation (5):

$$L=\sqrt{\alpha_c \tau_c} \quad (15)$$

Figure 2:
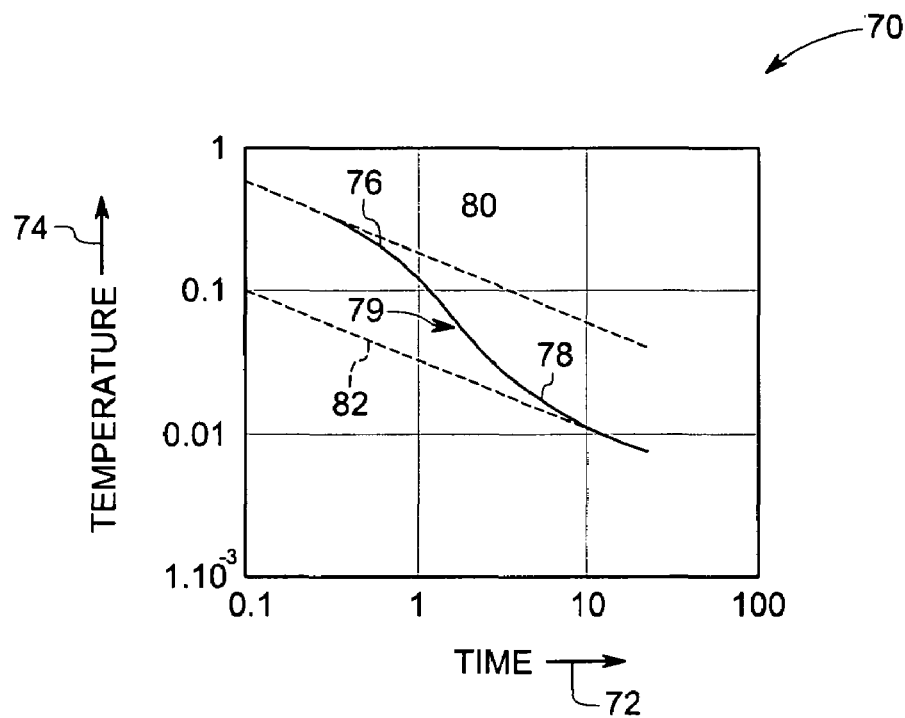
FIG. 2 is a simulated graphical representation of time-temperature responses of the coating and an substrate obtained using the system of FIG. 1.
Figure 3:
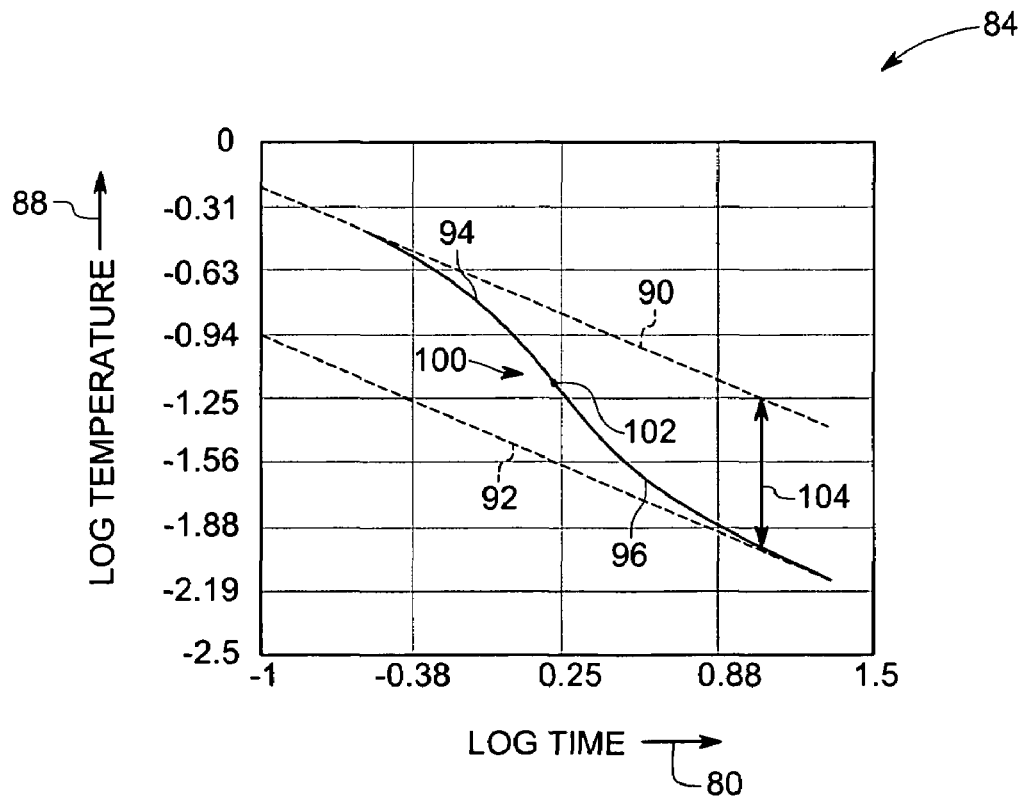
FIG. 3 is another simulated graphical representation of logarithms of time-temperature responses of the coating and the substrate obtained using the system of FIG. 1.

FIGS. 2-3 illustrate exemplary simulated time-temperature response graphs as obtained by the processor 34 described previously with reference to FIG. 1. FIG. 2 is a graphical representation 70, with X-axis showing time in seconds and denoted generally by reference numeral 72 and with Y-axis showing temperature in arbitrary units and denoted generally by reference numeral 74. Graph 70 illustrates a time-temperature response of the coating shown generally by reference numeral 76 and a time-temperature response of the substrate shown generally by reference numeral 78. As it can be seen from the graph 70, the curve 79 transitions continuously from a coating half-space shown by tangent 80 to a substrate half-space shown by tangent 82. This becomes even more clear in a log-log plot of temperature Vs time and is shown in FIG. 3.

FIG. 3, as mentioned above, is the log-log plot 84 of temperature Vs time on linear axes. The X-axis is denoted by reference numeral 86 and represents the log of time taken in seconds and the Y-axis denoted by reference numeral 88 represents the log of temperature in arbitrary units. The dotted line 90 is the coating half-space curve represented by equation (6). The lower dotted straight line 92 is the substrate half-space curve represented by equation (7), and equation (4) is the transition curve 100. FIG. 3, thus clearly illustrates that the portions of curve 100, denoted by reference numerals 94 and 96 have slopes equal to −½ on the log-log plot. The curve 100 also has a point of maximum slope 102, or inflection point (or inflection time "$t_{inflection}$"), between the two lines 90 and 92.

The second important feature in the graph 84 is the offset 104 between the two linear (in log-log) half-space curves. This offset, although a difference between lines 90 and 92 in log space, is a ratio in linear space and is defined as deltalog as described herein and given by equation (8). It will be appreciated by those skilled in the art that by taking the ratio of coating temperature over substrate temperature, everything cancels except the effusivities, as shown in equations (6) and (7). That is, the ratio depends only on the thermal characteristics of coating and substrate and not on the flash intensity. The substrate thermal characteristics is known or pre-determined. Hence, if the ratio is obtained experimentally, as shown as offset 104 in FIG. 3, the coating effusivity and thereby the reflectivity is also obtained.

Figure 4:
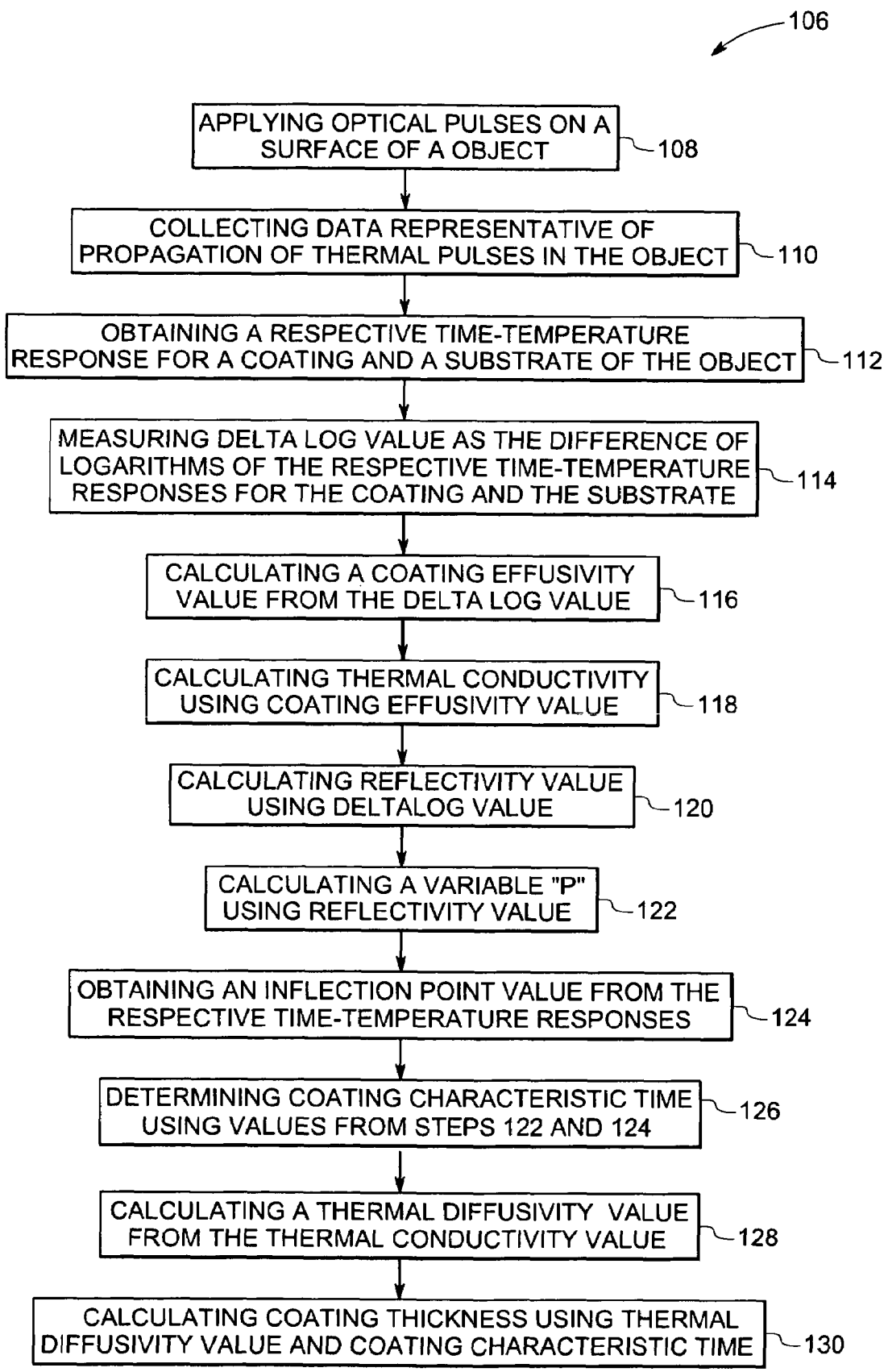
FIG. 4 is a flowchart illustrating exemplary steps for a non-destructive inspection method for determining thickness and thermal conductivity of an insulative coating, in accordance with an aspect of the present invention.

FIG. 4 is a flowchart 106 illustrating exemplary steps for a non-destructive testing or inspection method for determining thickness and thermal conductivity for an insulative coating. The method includes a step 108 for applying optical pulses on the surface of the object as described hereinabove with reference to FIG. 1. At step 110, the method includes obtaining data representative of a propagation of the thermal pulses in the surface of the object. At step 112, a respective time-temperature response for the coating and for the substrate is obtained from the data as shown in FIGS. 2 and 3.

One of the values that is obtained from the time-temperature responses at step 114 is the deltalog value as previously described in reference with equation (8) and is the difference of logarithms of the respective time-temperature responses for the substrate and for the coating. At step 116 a coating effusivity value is calculated from the deltalog value as given by equation (9). Then the thermal conductivity value is calculated at step 118 using the coating effusivity value as given by equation (3).

At step 120 a reflectivity value is calculated also using the deltalog value as given by equation (10). At step 122 a variable "p" is calculated using the reflectivity value as given by equation (12). At step 124 an inflection point "$t_{inflection}$" is obtained from the respective time-temperature responses. The inflection point is the point of maximum slope in the time-temperature response and is shown graphically in reference with FIG. 3. At step 126 a coating characteristic time is obtained from the inflection point "$t_{inflection}$" and the variable "p" as given by equation (11).

At step 128 a thermal diffusivity value for the coating, $\alpha_c$ is calculated using the thermal conductivity value as given by equation (13). The coating thickness value is finally calculated at step 130 using thermal diffusivity value and the coating characteristic time as given by equation (15). It may be noted by those skilled in the art that the thickness limit that can be determined using the technique described herein depends on availability of flash power and porosity of the coating.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. An apparatus for determining thickness and thermal conductivity for an insulative coating disposed on a substrate of an object, the apparatus comprising:
   a source for applying a plurality of optical pulses on a surface of the object, wherein the surface comprises the insulative coating;
   a filter disposed between the source and the object and configured to eliminate optical wavelengths greater than two microns emanating from the source;
   a recording system configured to collect data representative of a propagation of the plurality of optical pulses in the object, wherein the data comprises time-temperature responses; and
   a processor coupled to the recording system and configured to receive the data from the recording system and configured to determine a thickness value and a thermal conductivity value for the insulative coating.

2. The apparatus of claim 1, wherein the surface of the object comprises a dark peripheral coating disposed over the insulative coating.

3. The apparatus of claim 1, wherein the processor is configured to obtain time-temperature responses for the insulative coating and the substrate from the data received by the recording system.

4. The apparatus of claim 3, wherein the processor is configured to determine a reflectivity value and a coating characteristic time using time-temperature responses, and wherein the reflectivity value and the coating characteristic time are used to determine the thickness value and the thermal conductivity value.

5. The apparatus of claim 3, wherein the processor is configured to measure a deltalog value and an inflection point value from the respective time-temperature response.

6. The apparatus of claim 5, wherein the processor is configured to calculate a plurality of coating characteristic values using the deltalog value or the inflection point value.

7. The apparatus of claim 6, wherein the plurality of coating characteristic values comprise at least one of a coating effusivity value, a reflectivity value, a variable, a coating characteristic time, or a thermal diffusivity value.

8. The apparatus of claim 1, wherein the processor is configured to determine the thickness value and the thermal conductivity value simultaneously.

9. The apparatus of claim 1, wherein the insulative coating is at least one of thermally barrier coating (TBC) or environment baffler coating (EBC).

10. The apparatus of claim 1, wherein the source comprises one or more flash lamps.

11. The apparatus of claim 1, wherein the recording system comprises an infrared focal plane array camera.

12. A computer implemented nondestructive testing method for determining thickness and thermal conductivity for an insulative coating, the method comprising:
    obtaining a respective time-temperature response for the insulative coating and for a substrate from data representative of a propagation of a plurality of optical pulses in the insulative coating and the substrate, wherein the insulative coating is disposed on the substrate;
    measuring a deltalog value from the respective time-temperature responses;
    calculating a coating effusivity value from the deltalog value;
    calculating a thermal conductivity value from the coating effusivity value;
    calculating a reflectivity value from the deltalog value;
    determining a variable using the reflectivity value;
    measuring an inflection point value from the respective time-temperature response for the insulative coating and for the substrate;
    calculating a coating characteristic time using the inflection point value and the variable;
    calculating a thermal diffusivity value using the thermal conductivity value;
    determining a thickness value for the insulative coating from the thermal diffusivity value and the coating characteristic time; and
    outputting the thickness value and the thermal conductivity value to a computer display device or a printer or a combination thereof.

13. The method of claim 12, comprising obtaining the data representative of the propagation of the plurality of optical pulses in the insulative coating and the substrate.

14. The method of claim 12, comprising preparing a surface of the insulative coating by coating the surface with a dark peripheral coating.

15. The method of claim 12, wherein the thickness value and the thermal conductivity value is determined simultaneously.

16. The method of claim 12, wherein the insulative coating is at least one of thermally barrier coating (TBC) or environment barrier coating (EBC).

17. The method of claim 12, comprising irradiating the insulative coating by the plurality of optical pulses.

18. A computer implemented method for determining thickness and thermal conductivity for an insulative coating, the method comprising:
    obtaining a respective time-temperature response for the insulative coating and for a substrate, wherein the insulative coating is disposed on the substrate;
    measuring a deltalog value from the respective time-temperature responses;
    measuring an inflection point value from the respective time-temperature response for the insulative coating and for the substrate;
    calculating a plurality of coating characteristic values using the deltalog value or the inflection point value;
    determining a thermal conductivity value or a coating thickness value using one or more of the plurality of coating characteristic values; and
    outputting the thickness value and the thermal conductivity value to a computer display device or a printer or a combination thereof.

19. The method of claim 18, the plurality of coating characteristic values comprising at least one of a coating effusivity value, a reflectivity value, a variable, a coating characteristic time, or a thermal diffusivity value.

20. The method of claim 18, comprising:
    obtaining data representative of a propagation of a plurality of optical pulses in a surface of an object, wherein the surface comprises the insulative coating; and
    obtaining the respective time-temperature response for the insulative coating and for the substrate from the data.

21. The method of claim 20, comprising irradiating the surface by the plurality of optical pulses.

22. The method of claim 20, comprising preparing the surface by coating the surface with a dark peripheral coating.

23. The method of claim 18, wherein the thickness value and the thermal conductivity value is determined simultaneously.

24. The method of claim 18, wherein the insulative coating is at least one of thermally barrier coating (TBC) or environment barrier coating (EBC).

25. A tangible medium, comprising:
    code for obtaining a respective time-temperature response for an insulative coating and for a substrate, wherein the insulative coating is disposed on the substrate;
    code for measuring a deltalog value from the respective time-temperature responses;
    code for measuring an inflection point value from the respective time-temperature response for the insulative coating and for the substrate;
    code for calculating a plurality of coating characteristic values using the deltalog value or the inflection point value;
    code for determining a thermal conductivity value or a coating thickness value using one or more of the plurality of coating characteristic values; and
    code for outputting the thickness value and the thermal conductivity value to a computer display device or a printer or a combination thereof,
    wherein the tangible medium is configured for determining thickness and thermal conductivity for the insulative coating, and wherein the tangible medium is a computer-readable medium.

26. The tangible medium of claim 25, the plurality of coating characteristic values comprising at least one of a coating effusivity value, a reflectivity value, a variable, a coating characteristic time, or a thermal diffusivity value.

27. The tangible medium of claim 25 comprising:
    code for obtaining data representative of a propagation of a plurality of optical pulses in a surface of an object, wherein the surface comprises the insulative coating; and
    code for obtaining the respective time-temperature response for the insulative coating and for the substrate from the data.

28. An apparatus for determining thickness and thermal conductivity for an insulative coating disposed on a substrate of an object, the apparatus comprising:
    a source for applying a plurality of optical pulses on a surface of the object, wherein the surface comprises the insulative coating;
    a recording system configured to collect data representative of a propagation of the plurality of optical pulses in the object, wherein the data comprises time-temperature responses; and a processor coupled to the recording system and configured to receive the data from the recording system, the processor configured to determine a reflectivity value and a coating characteristic time using time-temperature responses, wherein the processor is configured to determine a thickness value and a thermal conductivity value for the insulative coating using the reflectivity value and the coating characteristic time.

29. An apparatus for determining thickness and thermal conductivity for an insulative coating disposed on a substrate of an object, the apparatus comprising:

a source for applying a plurality of optical pulses on a surface of the object, wherein the surface comprises the insulative coating;

a recording system configured to collect data representative of a propagation of the plurality of optical pulses in the object, wherein the data comprises time-temperature responses; and a processor coupled to the recording system and configured to receive the data from the recording system, the processor configured to determine a reflectivity value and a coating characteristic time using time-temperature responses, wherein the processor is configured to measure a deltalog value and an inflection point value from the respective time-temperature response.

30. The apparatus of claim 29, wherein the processor is configured to calculate a plurality of coating characteristic values using the deltalog value or the inflection point value.

31. The apparatus of claim 30, wherein the plurality of coating characteristic values comprise at least one of a coating effusivity value, a reflectivity value, a variable, a coating characteristic time, or a thermal diffusivity value.

32. A computer implemented nondestructive testing method for determining thickness and thermal conductivity for an insulative coating, the method comprising:

obtaining a respective time-temperature response for the insulative coating and for a substrate from data representative of a propagation of a plurality of optical pulses in the insulative coating and the substrate, wherein the insulative coating is disposed on the substrate;

measuring a deltalog value, an inflection point value, or a combination thereof, from the respective time-temperature responses;

calculating a coating effusivity value, or a coating characteristic time, or a combination thereof;

calculating a thermal conductivity value using the respective time-temperature response for the insulative coating and for the substrate;

calculating a thermal diffusivity value using the thermal conductivity value;

determining a thickness value for the insulative coating using the thermal diffusivity value; and outputting the thickness value and the thermal conductivity value to a computer display device, or a printer, or a combination thereof.

33. The method of claim 32, comprising calculating a reflectivity value from the deltalog value and determining a variable using the reflectivity value.

34. A computer implemented method for determining thickness and thermal conductivity for an insulative coating, the method comprising:

obtaining a respective time-temperature response for the insulative coating and for a substrate, wherein the insulative coating is disposed on the substrate;

calculating a plurality of coating characteristic values using the respective time-temperature response for the insulative coating and for the substrate;

determining a thermal conductivity value and a coating thickness value using one or more of the plurality of coating characteristic values, wherein the coating characteristic values are based on a deltalog value, an inflection point value, or a combination thereof; and outputting the thermal conductivity value and the coating thickness value to a computer display device, or a printer, or a combination thereof.

35. The method of claim 34, wherein the plurality of coating characteristic values comprise a coating effusivity value, a coating characteristic time, or a thermal diffusivity value, or a combination thereof.

36. An apparatus for determining thickness and thermal conductivity for an insulative coating disposed on a substrate of an object, the apparatus comprising:

a heat source configured for heating a surface of the object, wherein the surface comprises the insulative coating;

a recording system configured to collect data representative of a propagation of a plurality of thermal pulses in the object, wherein the data comprises time-temperature responses; and a processor coupled to the recording system and configured to use time-temperature responses to determine a thickness value and a thermal conductivity value for the insulative coating;

wherein the processor is configured to measure a deltalog value, and an inflection point value, from respective time temperature responses.

37. The apparatus of claim 36, wherein the processor is configured to calculate one or more coating characteristic values, wherein the coating characteristic values are based on a coating effusivity value, a reflectivity value, a coating characteristic time, and a thermal diffusivity value.

38. The apparatus of claim 36, wherein the processor is configured to calculate one or more coating characteristic values, wherein the coating characteristic values are based on a coating effusivity value, a coating characteristic time, or a thermal diffusivity value, or a combination thereof.

* * * * *

UNITED STATES PATENT AND TRADEMARK OFFICE
CERTIFICATE OF CORRECTION

| | |
|---|---|
| PATENT NO. | : 7,409,313 B2 |
| APPLICATION NO. | : 11/305438 |
| DATED | : August 5, 2008 |
| INVENTOR(S) | : Ringermacher et al. |

Page 1 of 1

It is certified that error appears in the above-identified patent and that said Letters Patent is hereby corrected as shown below:

In Column 9, Line 3, in Claim 9, delete "baffler" and insert -- barrier --, therefor.

Signed and Sealed this

Thirtieth Day of June, 2009

JOHN DOLL
*Acting Director of the United States Patent and Trademark Office*